(12) United States Patent
Zecchino et al.

(10) Patent No.: US 11,896,691 B1
(45) Date of Patent: Feb. 13, 2024

(54) UNIVERSAL MINERAL BASED SUNSCREEN

(71) Applicants: Julius Zecchino, New York, NY (US); Marina Turso, River Edge, NJ (US)

(72) Inventors: Julius Zecchino, New York, NY (US); Marina Turso, River Edge, NJ (US)

( * ) Notice: Subject to any disclaimer, the term of this patent is extended or adjusted under 35 U.S.C. 154(b) by 0 days.

(21) Appl. No.: 18/094,811

(22) Filed: Jan. 9, 2023

(51) Int. Cl.
*A61K 8/27* (2006.01)
*A61K 8/29* (2006.01)
*A61Q 17/04* (2006.01)
*A61K 8/19* (2006.01)

(52) U.S. Cl.
CPC ............ *A61K 8/19* (2013.01); *A61Q 17/04* (2013.01); *A61K 2800/42* (2013.01); *A61K 2800/48* (2013.01); *A61K 2800/522* (2013.01)

(58) Field of Classification Search
None
See application file for complete search history.

(56) References Cited

U.S. PATENT DOCUMENTS

| | | | |
|---|---|---|---|
| 2,255,607 A | 9/1941 | Ayers et al. | |
| 5,221,342 A | 6/1993 | Minami et al. | |
| 5,605,894 A * | 2/1997 | Blank ................ | A61K 8/368 514/159 |
| 5,902,569 A | 5/1999 | Oshima et al. | |
| 5,904,918 A | 5/1999 | Sterphone et al. | |
| 5,143,722 A | 8/1999 | Hollenberg et al. | |
| 5,961,995 A | 10/1999 | Mishihama et al. | |
| 6,090,373 A | 7/2000 | Oshima et al. | |
| 6,235,270 B1 | 5/2001 | Ishii et al. | |
| 6,759,052 B1 | 7/2004 | Suzuki et al. | |
| 2011/0020414 A1 * | 1/2011 | Kunin ................... | A61Q 19/08 514/669 |
| 2013/0164229 A1 * | 6/2013 | Mendoza ............... | A61K 8/922 424/59 |
| 2014/0010769 A1 * | 1/2014 | Lomakin ................ | A61K 8/25 424/59 |

OTHER PUBLICATIONS

U.S. Appl. No. 09/764,027, Tan et al.
U.S. Appl. No. 10/363,664, Ishii et al.
U.S. Appl. No. 11/149,644, Wei et al.
U.S. Appl. No. 11/401,642, Fishman et al.
U.S. Appl. No. 11/301,421, Simard et al.
U.S. Appl. No. 11/931,473, Hollman et al.
U.S. Appl. No. 11/765,614, Hollman et al.
U.S. Appl. No. 11/931,534, Hollman et al.
U.S. Appl. No. 11/931,658, Hollman et al.
U.S. Appl. No. 11/931,415, Hollman et al.
U.S. Appl. No. 12/746,186, Ehlis et al.
U.S. Appl. No. 13/186,539, Hodgson et al.
U.S. Appl. No. 15/146,487, Vepuri et al.
U.S. Appl. No. 15/146,480, Vepuri et al.
U.S. Appl. No. 15/303,689, Ota et al.
U.S. Appl. No. 15/766,523, Horil et al.
U.S. Appl. No. 16/439,472, Hutson et al.
U.S. Appl. No. 17/392,659, Jeong et al.
U.S. Appl. No. 17/689,805, Hutson et al.
U.S. Appl. No. 17/604,821, Kanzaki et al.

* cited by examiner

*Primary Examiner* — Brian Gulledge
(74) *Attorney, Agent, or Firm* — Dan DelaRosa

(57) ABSTRACT

A universal mineral based sunscreen that is good for all skin colors and prevents any ashy visual appearance on all colors of skin.

13 Claims, No Drawings

UNIVERSAL MINERAL BASED SUNSCREEN

BACKGROUND

There are numerous benefits of having pigment containing materials in Mineral Sunscreen products. These benefits include masking the unsightly white residue mineral sunscreens eg. Titanium Dioxide and or Zinc Oxide; offering protection from harmful rays of visible light, blue light from devices etc.; and preventing unwanted hyperpigmentation of the skin. An article in the Harvard Health Publishing entitled "Tinted Sunscreens: Benefits Beyond the Attractive Glow" by Dr. Neera Nathan and Dr Dieter Manstein, contends that using a blend of Iron Oxides Red, Yellow and Black create the best effect. This creates a shade like many products on the market that attempts to hide the white residue from the sunscreens on a particular set of skin types. However, this also creates the need to have several shades of products to achieve the result on all skin types. None of which are truly desired but are more acceptable than the white cast of the sunscreens particularly on dark skin tones. These do not create a universal masking mode. They work more like make-up hiding imperfections than a universal maskant.

An article in the Society of Cosmetics Chemists Newsletter entitled "Formulating Mineral Sunscreens for People of Color" by Dr. Yun Shao also promotes the use of Mineral Sunscreens as superior protection over Organic sunscreens. It further points out that Zinc Oxide is less opaque and easier to formulate than TiO2. It underlines the problem of making acceptable looking products especially for people with darker complexions. They point out that Red iron oxide may help but is not the answer. They also recommend blending with other iron oxides and or titanated micas to improve the naturalness of the look. This article teaches using blends of different iron oxide colors and leads toward a product line that has multiple skus to address different skin colors.

The presently claimed invention focuses on a universal maskant system by only utilizing only red iron oxide as a masking agent with a dispersing agent. We have found that much less pigment is needed to titrate a universal acceptable product for all skins. From the lightest to the darkest, one iron oxide that can cover even the highest level of SPF protection, whether anhydrous, aqueous or combinations of emulsions or suspensions thereof. It is clear that the prior art, focusing on blends of different colors of iron oxide, teaches away from the presently claimed invention which only focuses on red iron oxide as a masking agent that is added to the formulation in an amount so that the masking agent conceals the mineral sunscreen and creating a universal formulation that can be used by all skin colors and prevent ashy skin for darker skin tones.

SUMMARY OF THE INVENTION

The following implementations and aspects thereof are described and illustrated in conjunction with ingredients, formulations and methods that are meant to be exemplary and illustrative, not limiting in scope. The presently claimed invention relates to a universal mineral based sunscreen that is good for all types of skin and prevents any ashy visual appearance on all colors of skin. These and other advantages will become apparent to those skilled in the relevant art upon a reading of the following descriptions.

In one embodiment, a formulation of the present invention comprises dimethicone, polysilicone-11, iron oxide, coco-caprylate/caprate, polyglyceryl-6 polyricinoleate, polyhydoxystearic acid, di-linoleic acid/butanediol co-polymer, disodium stearoyl glutamate, castor oil/IPDI copolymer, *Camellia sinensis* leaf extract, cholesterol, tartaric acid, tocopheryl acetate, squalane, *Amaranthus caudatus* seed oil, *Hordeum vulgare* extract, wheat germ oil, linoleic acid, mica, titanium dioxide, ascorbic acid, caprylic/capric triglyceride, stearalkonium bentonite, propylene carbonate, zinc oxide, polyhydroxystearic acid, polyglyceryl-3 polyricinoleate, isostearic acid, lecithin, and mixtures and combinations thereof.

In another embodiment, the formulation is used as a product selected from a group comprising of sunscreen, cosmetics with sunscreen, make-up with sunscreen, skin care products with sunscreen, and mixtures and combinations thereof. In a further embodiment, the formulation creates products that are universal for all skin colors.

In still another embodiment, a formulation of the present invention comprises at least one film forming agent, at least one masking agent, at least one barrier repair agent, at least one mineral sunscreen, and mixtures and combinations thereof.

In yet another embodiment, the film forming agent is used for creating feel, texture and locking the formulation onto the skin; the film forming agent is selected from group comprising of polysilicone-11, Dimethicone/Vinyl Dimethicone Cross polymer, Dimethicone cross polymer, Vinyl Dimethicone cross polymer, Hydrocarbon Silicone cross polymer, Polyglycolated cross polymer and mixtures and combinations thereof. The film forming agent leaves a silky smooth texture on the skin, allows the sunscreen to wear longer and provides some water resistency.

In still another embodiment, the formulation further comprises a dispersant for the film forming agent, selected from group comprising of dimethicone, cyclomethicones, alkylated silicones, hydrocarbons, esters, alkanes, and mixtures and combinations thereof. In another embodiment, the film forming agent and the dispersant for the film forming agent is from about 10% to about 70% of the formulation.

In a further embodiment, the masking agent is selected from group comprising of iron oxide, red iron oxide, synthetic red iron oxide, natural red iron oxide, cosmetic grade red iron oxide, titanated mica and mixtures and combinations thereof.

In still another embodiment, the formulation further comprises dispersing agent for the masking agent, selected from group comprising of coco-caprylate/caprate, polyglyceryl-6 polyricinoleate, polyhydoxystearic acid, di-linoleic acid/butanediol copolymer, disodium stearoyl glutamate, castor oil/IPDI copolymer, mineral oil, glycerin, butylene glycol, esters, linear and branched pentaerythritol tetraoctanoate, lecithin, and mixtures and combinations thereof.

In still a further embodiment, the masking agent and the dispersing agent for masking agent is from about 0.01% to about 5.00% of the formulation.

In another embodiment, the formulation further comprises antioxidant, selected from group comprising of *Camellia sinensis* leaf extract, tocopheryl acetate, ascorbic acid, ferulic acid, tocopherol, N-acetyl cysteine, and mixtures and combinations thereof. In a further embodiment, a formulation wherein the antioxidant is from about 0.1% to about 50.0% of the formulation.

In still another embodiment, the barrier repair agent is selected from group comprising of cholesterol, squalane, *Amaranthus caudatus* seed oil, *Hordeum vulgare* extract, wheat germ oil, ceramide 1, ceramide 2, ceramide 4, ceramide 7, and mixtures and combinations thereof. In still a further embodiment, a formulation wherein the barrier repair agent is from about 0.05% to about 5.0% of said formulation.

In another embodiment, the formulation further comprises skin toner, selected from group comprising of mica, titanium dioxide, timeron super red, and mixtures and combinations thereof. In a further embodiment, a formulation wherein at least one skin toner is from about 0.1% to about 5.0% of the formulation.

In still another embodiment, the formulation further comprises thickener/stabilizer, selected from group comprising of caprylic/capric triglyceride, stearalkonium bentonite, propylene carbonate, disteardimonium hectorite, organic hectorite derivatives, silica, and mixtures and combinations thereof. In still a further embodiment, the thickener/stabilizer is from about 0.5% to about 10.0% of the formulation.

In another embodiment, the mineral sunscreen is selected from group comprising of zinc oxide, titanium oxide, polyhydroxystearic acid, polyglyceryl-3 polyricinoleate, isostearic acid, lecithin, titanium dioxide, coated titanium dioxide, and mixtures and combinations thereof. In a further embodiment, the mineral sunscreen is from about 2.0% to about 40.0% of the formulation.

In still another embodiment, a formulation of the presently claimed invention further comprises an activator for the antioxidant, the activator is selected from group comprising of tartaric acid, salicylic acid, alpha hydroxy acid, beta hydroxy acid, and mixtures and combinations thereof; in another embodiment, the activator for the antioxidant is from about 0.0% to about 5.0% of the formulation.

In still a further embodiment, the masking agent is used to conceal the mineral sunscreen thereby providing a universal formulation that can be used by all different skin colors. In another embodiment, the masking agent is used to conceal the mineral sunscreen and prevent ashy skin. In a further embodiment, the formulation is used as a product selected from a group comprising of sunscreen, cosmetics with sunscreen, make-up with screen, skin care products with sunscreen, and mixtures and combinations thereof, the product is universal for all skin colors.

In still another embodiment, the masking agent is added to the formulation in an amount so that the masking agent conceals the mineral sunscreen so that the universal formulation can be used by all skin colors and prevent ashy looking skin.

In still a further embodiment, a formulation comprises zinc oxide, titanium dioxide, water based dispersant, anhydrous based dispersant, red iron oxide, titanted red iron oxide, and mixtures and combinations thereof.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessarily to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

Iron (III) oxide or ferric oxide is the inorganic compound with the formula $Fe_2O_3$. It is one of three main oxides of iron, the other two being iron (II) oxide (FeO) which is rare, and iron (II or III) xide ($Fe_3O_4$), which also occurs naturally as the mineral magnetite. Iron oxides are safe, gentle and non-toxic on the surface of the skin. Iron oxide may be added to mineral sunscreens in order to improve "white cast" or ashy skin, however, prior to this patent application, it is combined with other colors of iron oxide to create a blend.

The present invention uses only red iron oxide with a dispersing agent. There are various dispersing agents or blends that can be used with the red iron oxide to optimize this formulation making a universal sunscreen that can be used by all skin types and colors without the results of ashy skin. Iron oxide can also broaden the protection offered by mineral sunscreens into the UVA and visible light spectrums. Mineral sunscreen ingredients zinc oxide and titanium dioxide are better at protecting the skin from visible light than chemical sunscreens due to the fact that they reflect and scatter light. However, they do not offer sufficient visible light protection without the addition of iron oxide. While iron oxide is effective at absorbing all wavelengths of visible light, it is particularly effective in absorbing longer UVA radiation and blue light.

The present invention relates to multiple embodiments including the formulation set forth in Table 1. In one embodiment, the formulation comprises:

TABLE 1

| | Sunscreen Formulation 1 | |
| --- | --- | --- |
| Phase | Ingredients (INCI) | Percentage Range |
| A | Dimethicone & Polysilicone-11 | from about 0 to about 80% |
| A | Dimethicone | from about 0 to about 80% |
| A | Dimethicone | from about 0 to about 80% |
| B | Dimethicone & Polysilicone-11 | from about 0 to about 80% |
| B | Iron Oxide (CI 77491), Coco-Caprylate/Capriate, Polyglycerol 1-6 Polyricnoleate, Polyhydroxystearic Acid, Dilinoleic Acid/Butanediol Copolymer, Disodium Stearoyl Glutamate, Castor Oil/IPDI Copolymer | from about 0.01 to about 2.0% |
| C | Camellia Sinesis leaf Extract | from about 0 to about 10% |
| C | Cholesterol | from about 0 to about 2.0% |
| C | Tartaric Acid | from about 0.5 to about 10.0% |
| D | Tocopheryl Acetate | from about 0 to about 5.0% |
| D | Squalane, Amaranthus Caudatus Seed Oil, Hordeum Vulgare Extract, Triticum (Wheat) Germ Oil | from about 0 to about 5.0% |
| D | Linoleic Acid | from about 0 to about 5.0% |
| E | Mica, Titanium Dioxide (CI 77891) | from about 0 to about 10% |
| F | Ascorbic Acid | from about 0 to about 40% |
| G | Caprylic/Capric Triglyceride, Stearlkonium Bentonite, Propylene Carbonate | from about 0 to about 20% |
| G | Zinc Oxide, Caprylic/Capric Triglyceride, Polyhydroxystearic Acid, Poyglyceryl 1-3, Polyricinoleate, Isostearic Acid, Lecithin | from about 5 to about 50% |

In formulation 1, the first step is to admix dimethicone & polysilicone-11, dimethicone, dimethicone, to form Phase A. Then admix dimethicone & polysilicone-11, coco-caprylate/caprate, polyglyceryl-6 polyricinoleate, polyhydroxystearic acid, dilinoleic acid/butanediol copolymer, disodium stearoyl glutamate, castor oil/IPDI copolymer to form phase B. Then admix *Camellia sinesis* Leaf Extract, Cholesterol and Tartaric Acid to from Phase C. Then admix Tocopheryl Acetate, squalane, *Amaranthus caudatus* seed oil, *Hordeum vulgare* extract, wheat germ oil to form Phase D. Phase D comprises Linoleic Acid and Phase F comprises Mica and titanium Oxide. Then admix caprylic/capric triglyceride, stearalkonium bentonite, propylene carbonate, zinc oxide, polyhydroxystearic acid, polyglyceryl-3 polyricinoleate, isostearic acid, lecithin to form Phase G. Phases A, B, C, D, E, F and G are admixed until uniform.

In another embodiment, the present invention relates to multiple embodiments including the formulation set forth in Table 2. In another embodiment, the formulation comprises:

TABLE 2

Sunscreen Formulation 2

| Phase | Ingredients (INCI) | Percentage |
|---|---|---|
| A | Dimethicone & Polysilicone-11 | from about 25 to about 75% |
| B | Iron Oxide (CI 77491), Coco-Caprylate/Capriate, Polyglycerol 1-6 Polyricnoleate, Polyhydroxystearic Acid, Dilinoleic Acid/Butanediol Copolymer, Disodium Stearoyl Glutamate, Castor Oil/IPDI Copolymer | from about 0.01 to about 5.0% |
| C | Zinc Oxide, Caprylic/Capric Triglyceride, Polyhydroxystearic Acid, Poyglyceryl 1-3, Polyricinoleate, Isostearic Acid, Lecithin | from about 5 to about 75% |

In another embodiment of formulation 2, Phase A is dimethicone & polysilicone-11. Then admix Iron Oxide, Coco-Caprylate/Capriate, Polyglycerol 1-6 Polyricinoleate, Polyhydroxystearic Acid, Dilinoleic Acid/Butanediol Copolymer, Disodium Stearoyl Glutamate, Castor Oil/IPDI Copolymer to form Phase B. Then admix Zinc Oxide, Caprylic/Capric Triglyceride, Polyhydroxystearic Acid, Polyglyceryl 1-3, Polyricinoleate, Isostearic Acid, Lecithin to form Phase C. Phases A, B and C are admixed until uniform.

In a further embodiment, the present invention relates to multiple embodiments including the formulation set forth in Table 3. In a further embodiment, the formulation comprises:

TABLE 3

Sunscreen Formulation 3

| Phase | Ingredients (INCI) | Percentage |
|---|---|---|
| A | Dimethicone & Polysilicone-11 | from about 25 to about 75% |
| B | Red Iron Oxide | from about 0.001 to about 2.0% |
| C | Zinc Oxide, | from about 5 to about 50% |

TABLE 3-continued

Sunscreen Formulation 3

| Phase | Ingredients (INCI) | Percentage |
|---|---|---|
| | Caprylic/Capric Triglyceride, Polyhydroxystearic Acid, Poyglyceryl 1-3, Polyricinoleate, Isostearic Acid, Lecithin | |

In formulation 3, Phase A is dimethicone & polysilicone-CI. Phase 2 is red iron oxide. Then admix Zinc Oxide, Caprylic/Capric Triglyceride, Polyhydroxystearic Acid, Polyglyceryl 1-3, Polyricinoleate, Isostearic Acid, Lecithin to form Phase C. Phases A, B and C are admixed until uniform.

In still another embodiment, the present invention relates to multiple embodiments including the formulation set forth in Table 4. In still another embodiment, the formulation comprises:

TABLE 4

Sunscreen Formulation 4

| Phase | Ingredients (INCI) | Percentage |
|---|---|---|
| A | Water | from about 10 to about 90% |
| A | Butylene Glycol | from about 0 to about 80% |
| A | Benzyl Alcohol, Salicylic Acid, Glycerin, Sorbic Acid | from about 0 to about 20% |
| A | Water, Boswellia Serrata Extract, Centella Asiatica Extract, Betula Alba Bark Extract, Polygonum Cuspidatum Root Extract | from about 0 to about 10% |
| A | Simethicone | from about 0 to about 5% |
| A | Tromethamine | from about 0 to about 5% |
| A | Polysorbate 20 (polyoxyethalene sorbitan monolaurate) | from about 0 to about 10% |
| B | Alkyl Benzoate | from about 0 to about 90% |
| B | Coco-Caprylate/Caprate | from about 0 to about 90% |
| B | Ethylhexyl Palmitate | from about 0 to about 90% |
| B | Polyglyceryl-6 Polyricinoleate, Polyglyceryl-10 Dioleate | from about 0 to about 20% |
| B | Zinc Oxide, Caprylic/Capric Triglyceride, Polyhydroxystearic acid | from about 5 to about 50% |
| B | Lecithin | from about 0 to about 5% |
| B | Isododecane, Disteardimonium Hectorite, Propylene Carbomate | from about 0 to about 40% |
| B | Dimethicone, Polysilicone-11, Butyrospermum Parkii (Shea) | from about 0 to about 75% |
| B | Isododecane, Polymethylsilsequioxane, Trimethylsilooxysilicate | from about 0 to about 40% |
| B | C18-36 Acid Triglyceride | from about 0 to about 90% |
| B | Divinyldimethicone, Dimethicone, Phenylsilsesquioxane Cross Polymer | from about 0 to about 90% |

In formulation 4, admix water, Butylene Glycol, Benzyl Alcohol, Salicylic Acid, Glycerin, Sorbic Acid, Water, *Boswellia serrata* Extract, *Centella asiatica* Extract, *Betula Alba* Bark Extract, *Polygonum Cuspidatum* Root Extract, Simethicone, Tromethamine, and Polysorbate 20, polyoxyethylene sorbitan mono laurate to form Phase A and heat to 70-75 degrees Celsius. Then admix Alkyl Benzoate, Coco-Caprylate/Caprate, Ethylhexyl Palmitate, Polyglyceryl-6

Polyricinoleate, Polyglyceryl-10 Dioleate, Zinc Oxide, Caprylic/Capric Triglyceride, Polyhydroxystearic acid, Lecithin, Isododecane, Disteardimonium Hectorite, Propylene Carbomate, Dimethicone, Polysilicone-11, Butyrospermum Parkii (Shea), Isododecane, Polymethylsilsesquioxane, Trimethylsilooxysilicate, Acid Triglyceride, Divinyldimethicone, Dimethicone, Phenylsilsesquioxane Cross Polymer to form Phase B and heat to 80-85 degrees Celsius. Admix Phases A and B until uniform and while maintaining a temperature of 80-85 degrees Celsius. Cool to room temperature while agitating.

In another further embodiment, the present invention relates to multiple embodiments including the formulation set forth in Table 5. In another further embodiment, the formulation comprises:

TABLE 5

Sunscreen Formulation 5

| Phase | Ingredients (INCI) | Percentage |
| --- | --- | --- |
| A | Gransil DM 5 LC: Dimethicone & Polysilicone-11 | from about 95 to about 50% |
| B | Zinc oxide blend | from about 5.00 to about 50% |
| C | Red Iron Oxide dispersed in pentaerythritol isostearate | from about 0.01 to about 5.0% |

In formulation 5, Phase A comprises Dimethicone & Polysilicone-11; Phase B comprises a Zinc oxide blend; and Phase C comprises Red Iron Oxide dispersed in pentaerythritol isostearate. Phases A, B and C are admixed until uniform.

In still yet another embodiment, the present invention relates to multiple embodiments including the formulation set forth in Table 6. In still yet another embodiment, the formulation comprises:

TABLE 6

Sunscreen Formulation 6

| Phase | Ingredients (INCI) | Percentage |
| --- | --- | --- |
| A | Gransil DM 5 LC: Dimethicone and Polysilicone-11 | from about 95 to about 75% |
| B | Zinc Oxide 100% powder | from about 5.0 to about 25% |
| C | Iron Oxide - Red | from about 0.01 to about 5.0% |

In formulation 6, Phase A comprises Dimethicone & Polysilicone-11; Phase B comprises a Zinc oxide powder and Phase C comprises Iron Oxide. Phases A, B and C are admixed until uniform.

The present invention relates to multiple embodiments including the formulation set forth in Table 7. In one embodiment, the formulation comprises:

TABLE 7

Sunscreen Formulation 7

| Phase | Ingredients (INCI) | Percentage |
| --- | --- | --- |
| A | Water | from about 10 to about 90% |
| B | Butylene Glycol | from about 0 to about 50% |
| C | Benzyl alcohol, salicylic acid, glycerin, sorbic acid | from about 0 to about 2% |
| D | Water & Boswellia Serrata & Centella Asiatica & Betula Alba bark Extracts & Polygonum Caspidadatum Root Extract | from about 0 to about 20% |
| E | Simethicone | from about 0 to about 5% |
| F | Tromethamine | from about 0 to about 5% |
| G | Polysorbate 20: Polyethylene Sorbitan Monlaurate | from about 0 to about 5% |
| H | C12-C15 Alkyl Benzoate | from about 0 to about 60% |
| I | Coco-Caprylate/Caprate | from about 0 to about 60% |
| J | Ethylexyl Pamitate | from about 0 to about 60% |
| K | Polyglyceryl-6 Polyrincinoleate, Polyglyceryl-10 Dioleate | from about 0 to about 10% |
| L | Zinc Oxide, Capryilic/Caprate Triglyceride, Polyhydroxystearic acid | from about 5 to about 50% |
| M | Gransperse CDS: Iron Oxides (CI 77491), Coco-Caprylate/Caprate, Polyglyceryl-6 Polyricinoleate, Polyhydroxystearic Acid, Dilinoleic Acid/Butanediol Copolymer, Castor Oil/IPDI Copolymer, and Disodium Stearoyl Glutamate | from about 0.01 to about 5.0% |
| N | Lecithin | from about 0 to about 2.0% |
| O | Isododecane, Disteardimonium Hectorite, Propylene Carbamate | from about 0 to about 20% |
| P | Gransil SIW-038: Dimethicone, Polysilicone-11, Butyrospermum Parkii (Shea) Butter, Water, Glycerin, and Decyl Glucoside | from about 0 to about 50% |
| Q | GranresinMQI T-50: Isododecane and Polymethylsilsesquioxane/Trimethylsiloxysilicate | from about 0 to about 10% |
| R | C18-C36 Acid Triglyceride | from about 0 to about 80% |
| S | Granpowder EDC: Divinyldimethicone/Dimethicone/Phenylsilsesquioxane Crosspolymer | from about 0 to about 10% |

In still yet another further embodiment, Phase B (Butylene Glycol) is admixed in Phase A (water). Then Phase C (Benzyl alcohol, salicylic acid, glycerin, sorbic acid) is admixed. Then Phase D (the mixture of Water & *Boswellia serrata* & *Centella asiatica* & *Betula alba* bark Extracts & *Polygonum caspidadatum* Root Extract) is admixed. Subsequently, Phase E (Simethicone), Phase F (Tromethamine), Phase G (Polyethylene Sorbitan Monlaurate), Phase H (Alkyl Benzoate), Phase I (Coco-Caprylate/Caprate) and Phase J (Ethylexyl Pamitate) are admixed into the overall mixture. Then, Phase K (Polyglyceryl-6 Polyrincinoleate, Polyglyceryl-10 Dioleate) is admixed. Phase L (Zinc Oxide, Capryilic/Caprate Triglyceride, Polyhydroxystearic acid) is subsequently admixed. Then Phase M (the mixture of Iron Oxide, Coco-Caprylate/Caprate, Polyglyceryl-6 Polyricinoleate, Polyhydroxystearic Acid, Dilinoleic Acid/Butanediol Copolymer, Castor Oil/IPDI Copolymer, and Disodium Stearoyl Glutamate) is admixed. Then Phase N (Lecithin) and Phase O (Isododecane, Disteardimonium Hectorite, Propylene Carbamate) are admixed. Phase P (the blend of Dimethicone, Polysilicone-11, Butyrospermum Parkii (Shea) Butter, Water, Glycerin, and Decyl Glucoside) is admixed. Phase Q (Isododecane and Polymethylsilsesquioxane/Trimethylsiloxysilicate), Phase R (Acid Triglyceride), and Phase S (Divinyldimethicone/Dimethicone/Phenylsilsesquioxane Crosspolymer) are admixed until the mixture is uniform.

Numerous modifications and variations of the present invention are possible in light of the above teachings. It is therefore to be understood that within the scope of the attendant claims attached hereto, this invention may be practiced otherwise than as specifically disclosed herein.

What is claimed is:

1. A formulation consisting of;
   at least one film forming agent used for creating feel, texture and locking said formulation onto the skin and selected from the group consisting of polysilicone-11, dimethicone/vinyl dimethicone crosspolymer, dimethicone crosspolymer, vinyl dimethicone crosspolymer, hydrocarbon silicone crosspolymer, polyglycolated crosspolymer, and mixtures and combinations thereof;
   at least one dispersant for said film forming agent selected from the group consisting of dimethicone, cyclomethicones, alkylated silicones, hydrocarbons, esters, alkanes, and, mixtures and combinations thereof;
   at least one masking agent selected from the group consisting of iron oxide, red iron oxide, synthetic red iron oxide cosmetic grade, natural red iron oxide cosmetic grade, titanated mica, and mixtures and combinations thereof;
   at least one dispersing agent for said masking agent selected from the group consisting of coco-caprylate/caprate, polyglyceryl-6 polyricinoleate, polyhydoxystearic acid, dilinoleic acid/butanediol copolymer, disodium stearoyl glutamate, castor oil/IPDI copolymer, mineral oil, glycerin, butylene glycol, esters, linear and branched pentaerythel tetraoctanoate, lecithin, and mixtures and combinations thereof;
   at least one antioxidant selected from the group consisting of *Camellia sinensis* leaf extract, tocopheryl acetate, ascorbic acid, ferulic acid, tocopheryl, N-acetyl cysteine, and mixtures and combinations thereof;
   an activator for said antioxidant, said activator selected from the group consisting of tartaric acid, salicylic acid, alphahydroxy acid, beta hydroxy acid, and mixtures and combinations thereof;
   at least one barrier repair agent selected from the group consisting of cholesterol, squalane, *Amaranthus caudatus* seed oil, hordeumvulgare extract, wheat germ oil, ceramide 1, ceramide 2, ceramide 4, ceramide 7, and mixtures and combinations thereof;
   at least one skin toner selected from the group consisting of mica, titanium dioxide, timeron super red, and mixtures and combinations thereof;
   at least one thickener/stabilizer selected from the group consisting of caprylic/capric triglyceride, stearalkonium bentonite, propylene carbonate, disteardimonium hectorite, organic hectorite derivatives, silica, and mixtures and combinations thereof;
   and at least one mineral sunscreen selected from the group consisting of zinc dioxide, polyhydroxystearic acid, polyglycervl-3 polyricinoleate, isostearic acid, lecithin, titanium dioxide, uncoated and coated titanium dioxide, and mixtures and combinations thereof.

2. The formulation of claim 1 wherein said at least one film forming agent and at least one dispersant for said at least one film forming agent are from about 10% to about 70% of said formulation.

3. The formulation of claim 1 wherein said at least one masking agent and at least one dispersant for said at least one masking agent for said masking agent are from about 0.05% to about 5.0% of said formulation.

4. The formulation of claim 1 wherein said at least one antioxidant is from about 0 to about 1.0% of said formulation.

5. The formulation of claim 1 wherein said at least one barrier repair agent is from about 0.05% to about 5.0% of said formulation.

6. The formulation of claim 1 wherein said at least one skin toner is from about 0 to about 5.0% of said formulation.

7. The formulation of claim 1 wherein said at least one thickener/stabilizer is from about 0.5% to about 10.0% of said formulation.

8. The formulation of claim 1 wherein said at least one mineral sunscreen is from about 2.0% to about 40.0% of said formulation.

9. The formulation of claim 1 wherein said activator for said at least one antioxidant is from about 0.0% to about 5.0% of said formulation.

10. The formulation of claim 1 wherein said at least one masking agent is used to conceal said at least one mineral sunscreen thereby providing a universal formulation that can be used by all different skin colors.

11. The formulation of claim 1 wherein said at least one masking agent conceals said at least one mineral sunscreen and thus prevents ashy skin.

12. The formulation of claim 1 wherein said formulation is used as a product selected from the group consisting of sunscreen, cosmetics with sunscreen, make-up with screen, skin care products with sunscreen, and mixtures and combinations thereof, said product is universal for all skin colors.

13. The formulation of claim 1 wherein said masking agent is added to said formulation in an amount so that said masking agent conceals said mineral sunscreen so that said formulation can be used by all skin colors and prevent ashy skin.

* * * * *